(12) United States Patent
Kumar et al.

(10) Patent No.: US 6,736,834 B1
(45) Date of Patent: May 18, 2004

(54) RESORBABLE IMPLANT HEATING DEVICE

(75) Inventors: Mukesh Kumar, Warsaw, IN (US); H. Gene Hawkins, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 88 days.

(21) Appl. No.: 10/074,738

(22) Filed: Oct. 29, 2001

(51) Int. Cl.$^7$ ................................................ A61F 7/12
(52) U.S. Cl. .......................................... 607/96; 607/114
(58) Field of Search .......................... 607/96, 108, 184, 607/110, 111, 112, 114; 602/2, 14; 604/291; 383/901

(56) References Cited

U.S. PATENT DOCUMENTS

| | | | | |
|---|---|---|---|---|
| 3,014,117 A | * | 12/1961 | Madding | 392/443 |
| 4,103,147 A | * | 7/1978 | Carvalho | 219/524 |
| 4,372,318 A | * | 2/1983 | Viesturs et al. | 607/109 |
| 4,688,572 A | * | 8/1987 | Hubbard et al. | 607/112 |
| 4,700,706 A | * | 10/1987 | Munch | 607/96 |
| 5,020,711 A | * | 6/1991 | Kelley | 224/222 |
| 5,050,596 A | * | 9/1991 | Walasek et al. | 607/111 |
| 5,148,804 A | * | 9/1992 | Hill et al. | 607/108 |
| 5,476,442 A | * | 12/1995 | Madej | 602/26 |
| 5,507,794 A | * | 4/1996 | Allen | 607/112 |
| 5,545,198 A | | 8/1996 | Owens | |
| 5,823,984 A | * | 10/1998 | Silverberg | 602/61 |
| 6,231,596 B1 | * | 5/2001 | Collins | 607/114 |
| 6,537,308 B2 | * | 3/2003 | Burkhart | 607/109 |

* cited by examiner

Primary Examiner—Linda C. M. Dvorak
Assistant Examiner—Aaron Roane
(74) Attorney, Agent, or Firm—Harness, Dickey & Pierce, P.L.C.

(57) ABSTRACT

A heating device for maintaining an elevated temperature of a polymer resorbable implant is disclosed. The heating device has a pair of members coupled by a hinge. At least one of the members defines a sealed cavity containing a heated liquid which maintains the temperature of the resorbable polymer implant above the implant's glass transition temperature. The members of the device being rotatable about a hinge to allow encapsulation of the resorbable implant adjacent to the heat bearing liquid while maintaining a separation between the liquid and the implant device.

13 Claims, 4 Drawing Sheets

RESORBABLE IMPLANT HEATING DEVICE

BACKGROUND OF THE INVENTION

1. Field of the Invention

This invention generally relates to an apparatus and method for heating a resorbable implant, and more particularly, to a method and apparatus for heating a resorbable implant which is reusable and provides a method for heating to thereby soften the resorbable implant prior to surgical implantation.

2. Discussion of the Related Art

The repair of separated or dislocated bone fragments or segments following bone surgeries sometimes requires realignment of the separated or dislocated fragments or segments and subsequent secure fixation for promoting proper natural rejoinder of these bone fragments or segments. The presence of relative motion of the bone fragments or segments at a fracture or osteotomy location may result in irritation of the surrounding tissues, nonunion between the bone fragments, and an extension of the time for fracture healing. It is therefore desirable to accomplish as completely as possible an immobilization of the fracture or osteotomy site. This involves the relative fixation of affected bone segments relative to each other and in relation to the surrounding bone structure.

Known methods for providing fixation between adjacent bone portions have included the use of metallic plates of varying configurations, which are secured across osteotomies or fracture sites by metallic bone screws. These devices have been made of biocompatible metals and metal alloys, such as commercially pure titanium, stainless steel and cobalt chrome molybdenum. Other materials and devices, such as wires, intramedullary nails or externally fixed pins have also been used to reduce bone fracture mobility and to improve the relative position of adjacent segments. The aim of fixation of adjacent bone portions is to immobilize the fracture or osteotomy sites in order to promote localized bone growth in the natural repair of the separation.

The use of medical implant devices made from bioresorbable materials has been described in literature and these devices have the advantage of being absorbed by the body over a period of time so as to allow for bone or fibrous material to become repaired at a fracture or osteotomy site by growing into the space created between adjacent bone portions. Many bioresorbable materials have been suggested for use in fixation of adjacent bone portions. It was believed that these materials had to be extremely strong to fixate the bone portions over a relatively long period of time. This typically meant that the osteosynthesis plate had to be relatively thick and be made out of a high molecular weight oriented material such as poly L-lactic acid in which the molecular weight would exceed 250,000. See Pihlajamaki, H., et al., "Absorbable Pins of Self-Reinforced Poly-L-Lactic Acid for Fixation of Fractures and Osteotomies," Journal of Bone and Joint Surgery, v. 74-B, n. 6, p. 853–857, November 1992. In addition, it was believed that certain copolymers of glycolide and lactide were not appropriate for use in osteosynthesis plates because of a rapid loss of mechanical strength. Grijpma, D. W., et al., "Poly (L-lactide) Crosslinked with Spiro-bis-dimethylene-carbonate," Polymer, v. 34, n. 7, 1993 at 1496.

One resorbable material of particular interest is marketed by Biomet, Inc. (Warsaw, Ind.) under the tradename LACTOSORB®. LACTOSORB® is an absorbable co-polymer synthesized from all-natural ingredients: 82% L-lactic acid and 18% glycolic acid, unlike the homopolymers in common use such as 100% poly-L-lactic acid (PLLA) or 100% poly-glycolic acid (PGA), LACTOSORB® copolymer is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of it's strength for six to eight weeks, which is appropriate for healing, but not so long as to raise concerns about long-term stress shielding of bone.

These polymeric resorbable devices may require "molding in the operating room" before they can be implanted. By way of non-limiting example, the minimum temperature for achieving a moldable condition generally is above the glass transition temperature (Tg) (approximately 57/60° C.). During the heating stages of the resorbable materials, it is best not to allow the device (or any device possibly affected by water) to come in direct contact with boiling water. Because of this, It is difficult to raise the temperature of the resorbable device to above its glass transition temperature and to maintain the device above its glass transition temperature for long enough periods of time in the operating room to allow interoperative implant shape changes.

A need, therefore, exists for an apparatus and system which can raise a resorptive polymer material implant to above its glass transition temperature without exposing the implant directly to a liquid phase material. A need further exists for an apparatus and system which allows the resorbable material to be maintained above its glass transition temperature for an extended period of time. Further, a need exists for a heating device which is sterilizeable, as well as resusable.

SUMMARY OF THE INVENTION

In accordance with the teaching of the present invention, a device capable of heating resorbable material is disclosed having a pair of generally planar members. Each planar member defines at least one cavity which contains heatable fluid. The generally planar members are coupled by a hinge which allow the members to be rotated adjacent to each other so as to hold the resorbable polymer implant in close proximity to the heatable fluid. The temperature of the liquid stored within the cavity is elevated to above the glass transition temperature of a resorbable polymer. The resorbable polymer component which is to be surgically implanted in a patient is placed between the folded members and absorbs heat from the liquid stored within the cavity.

In one preferred embodiment, each member defines a shallow dish portion. Disposed above the shallow dish portion is a flexible polymer member which defines a fluid filled cavity therebetween. The fluid filled cavities are disposed adjacent to each other when the members are folded about the hinge, thereby holding the resorbable polymer component between two flexible polymer members, thereby increasing the surface area of the component in close proximity to the liquid.

In yet another preferred embodiment, the members define a cavity which is capable of accepting a fluid filled bag into a slot. The fluid filled bags can be heated prior to incorporation into the members through the slot.

In yet another preferred embodiment, the fluid filled bags are fastened to one surface of the foldable members using standard fabric fasteners. As with the other system, the fluid filled bag may be heated either prior to or after its adjoinment with the members.

The present invention provides a device which is capable of heating a resorbable surgical component and maintaining it above its glass transition temperature. The devices contain at least one fluid filled flexible sack, which functions to store heat energy to be transferred to the resorbable material through the flexible sack without submerging the resorbable material in a liquid. As a result, the aforementioned disadvantages associated with currently available resorbable material heating systems have been substantially reduced or eliminated.

BRIEF DESCRIPTION OF THE DRAWINGS

The various advantages of the present invention will be apparent to one skilled in the art upon reading the following specifications and by reference to the drawings in which.

DETAILED DESCRIPTION OF THE PREFERRED EMBODIMENTS

The following description of the preferred embodiments is merely exemplary in nature and is in no way intended to limit the invention, its application, or uses. Moreover, while various specific structures are disclosed, it will be understood by those skilled in the art that they are merely exemplary and other specific structures may be used.

Figure 1:
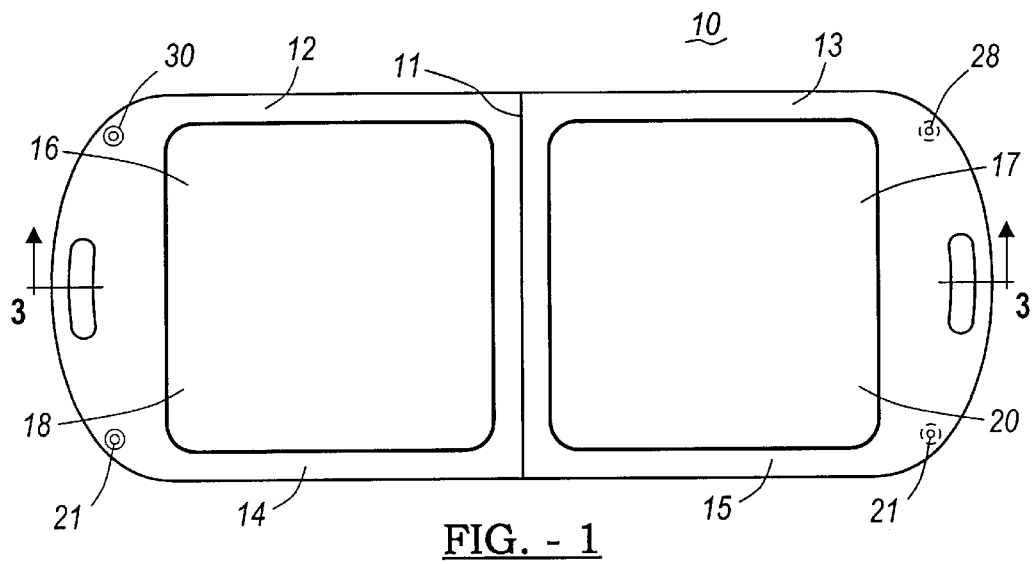
FIGS. 1–4 represent the resorbable implant heating device of the current invention.
Figure 2:
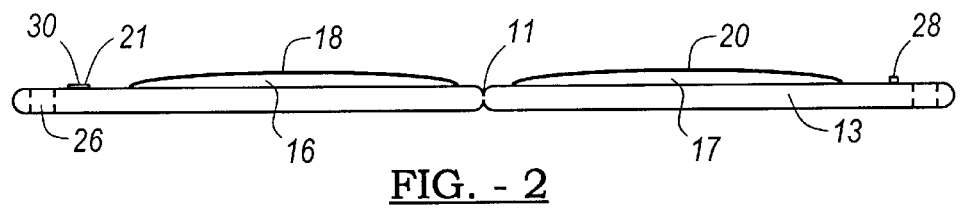
Figure 3:
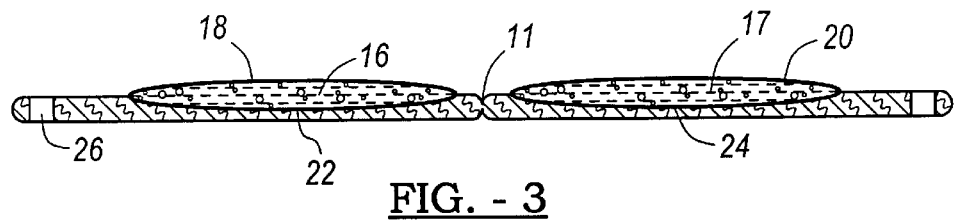

FIGS. 1–3 disclose a first embodiment of a resorbable implant heating device 10 of the present invention. The resorbable implant heating device 10 is formed of a first member 12 and second member 13 which are coupled by a hinge 11. Disposed on a first and second surface 14 and 15 of the first and second members 12 and 13 are first and second fluidized compartments 16 and 17. The fluidized compartments 16 and 17 are formed by a first and second elastic or flexible members 18 and 20 and first and second concave surface 22 and 24 which are disposed within the first and second surfaces 14 and 15. The first and second elastic or flexible members 18 and 20 are sealed to the perimeter of the generally concave surfaces to form a cavity to encapsulate a liquid which is saline or another appropriate liquid. Further disposed within the first and second members 12 and 13 are a pair of handles 26 which are used to carry the resorbable implant heating device 10 during a surgical procedure. Defined on the first and second surface 14 and 15 are a plurality of fastening devices 21 to hold the first and second surfaces 14 and 15 together and generally parallel to each other after rotating about hinge 11. Shown are male and female components 28 and 30 of the fastening devices 21. It should be envisioned that any other coupling structure such as a hook and eye, snap, VELCRO®, etc. would be equally applicable.

Figure 4:
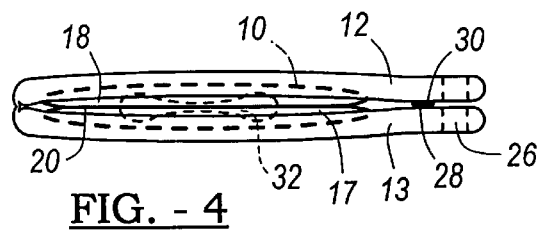

FIG. 4 depicts the use of the resorbable implant heating device 10 as contemplated. As shown, the first member 12 is rotated about hinge 11 so the first and second fluidized compartments 16 and 17 are disposed adjacent to each other. Located between the first and second elastic or flexible members 18 and 20 is the resorbable polymer implant 32 to be heated. It is envisioned that the entire resorbable implant heating device 10 can be placed into an autoclave or microwave or other heating apparatus to bring the fluid which is stored within the first and second fluidized compartments 16 and 17 up above the glass transition temperature of the resorbable polymer implant 32. Either prior to or after the heating of the liquid, the resorbable implant 32 is placed onto the second elastic membrane 20 and the first member 12 is rotated about hinge 11 into place. Upon encountering the second member 13, the female portion 30 of the fastener 21 is coupled to the male portion 28 to lock the two devices together. As can be seen, the handles 26 facilitate easy movement of the resorbable implant heating device 10 about the operating room.

Figure 5:
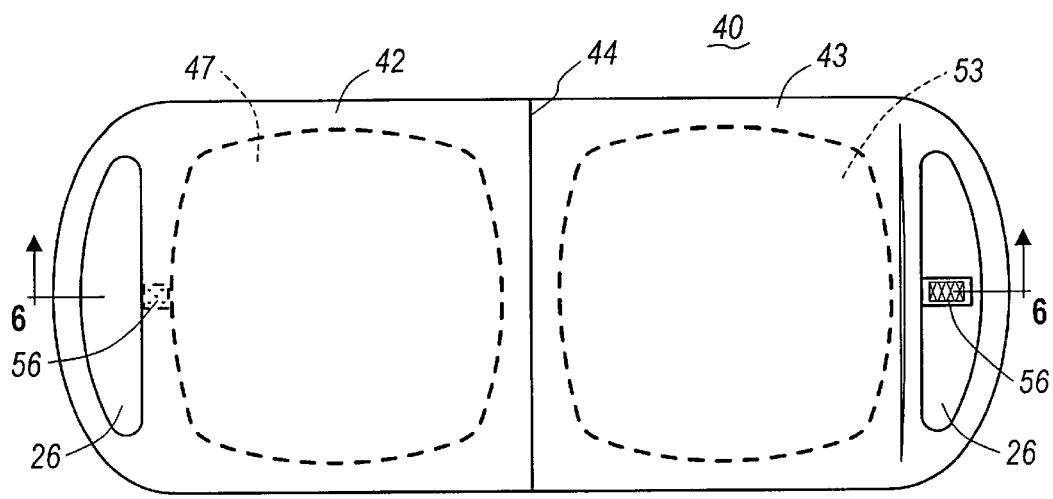
FIGS. 5–7 represent a second embodiment of the resorbable implant heating device of the current invention.
Figure 6:
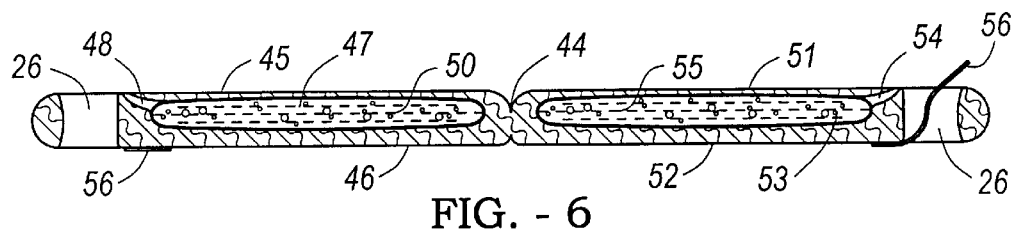
Figure 7:
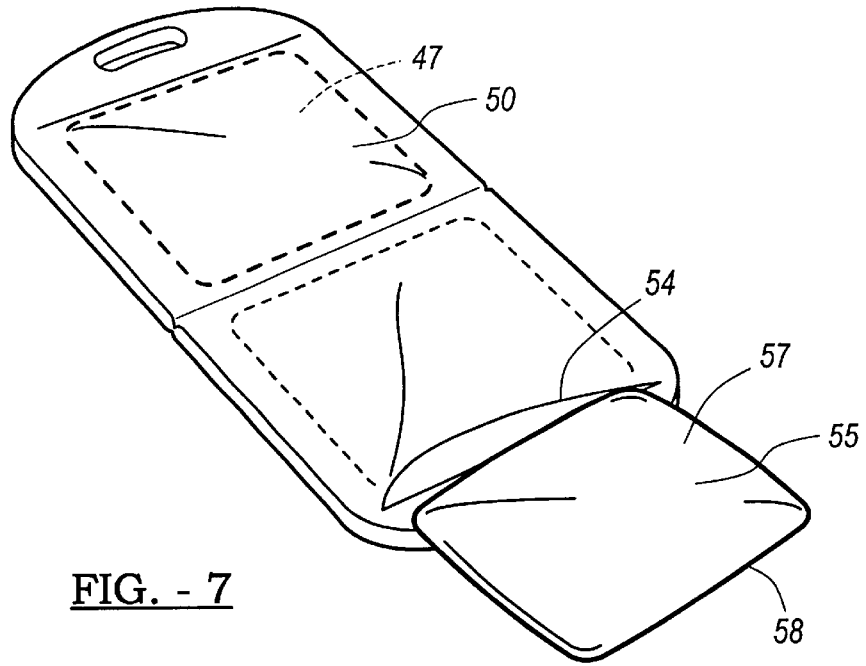

FIGS. 5–7 depict another preferred embodiment of the present invention. As shown in FIG. 5, the resorbable implant heating device 40 has a pair of generally planar members 42 and 43 coupled together by hinge 44. Similar to the device shown in FIGS. 1–4, the members 42 and 43 can define a pair of handles 26 for ease of movement of the device 40. Shown is a VELCRO® fastener 56 which can be used to adjustably fasten the handles together.

FIG. 6 depicts a cross-section of the resorbable implant heating device 40. As is shown, the first member 42 has a inner surface 45 and an outer surface 46. Defined between the inner and outer surfaces 45 and 46 is a cavity 47. The cavity 47 is accessible, via slot 48, defined in the inner surface 45. Disposed within the cavity 47 is a fluid filled bag 50. Optionally, similar structures can be defined in member 43. Further depicted are the inner surface 51 and outer surface 52. Defined between the surfaces 51 and 52 is the cavity 53 which holds a fluid filled bag 55. As can be seen in FIG. 7, the fluid filled bag 55 can be inserted into the structure through slot 54 defined in the first surface 51.

Figure 8:
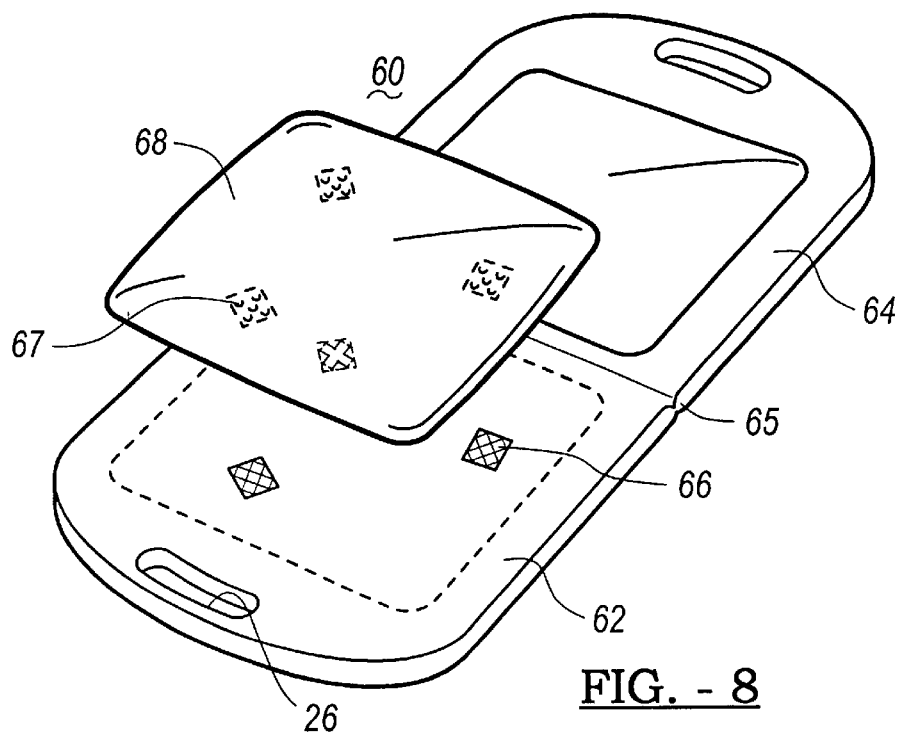
FIGS. 8–9 represent yet another embodiment of the present invention.
Figure 9:
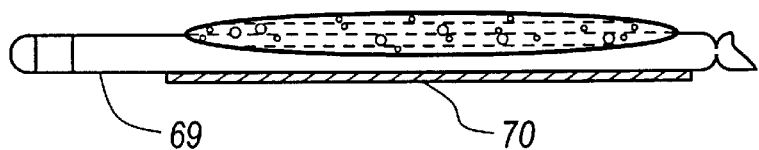

FIGS. 8–9 depict yet another embodiment of the present invention. Shown is a resorbable implant heating device 60 having first and second halves 62 and 64 separated by a hinge mechanism 65. Each of the members 62 and 64 has a plurality of fastening devices 66 which couple to fastening devices 67 on the fluidized bag 68. While it is envisioned that the non-implant conducting surfaces of the first and second members 12 and 13 would have insulating properties, FIG. 9 shows a lower surface 69 having a layer of insulating material 70 to assist in the retention of heat in the resorbable implant heating device.

It is envisioned that the elastic members 18 and 20 of resorbable implant heating device 10, the fluid filled bag 55 of the heating device 40, and the fluidized bag 68 of heating device 60 be formed of a autoclavable material which remains flexible such as silicone. It is preferable that the liquid stored beneath these layers have a high boiling point of greater than about 220° F. and a high specific heat. It is further preferable that the contact surface of each heating device in relation to the implant be configured of a material having a high heat transfer coefficient. The resorbable implant heating devices 10, 40, or 60 could each be inserted into an autoclave or a microwave generating device to heat the fluid within. The structural material of the first and second members 12 and 13 or 42 and 43 for either resorbable implant heating device 10 or 40 can be made of a relatively rigid insulating material to trap the heat within the fluidized compartments 16 and 17 or 47 and 53.

Figure 10:
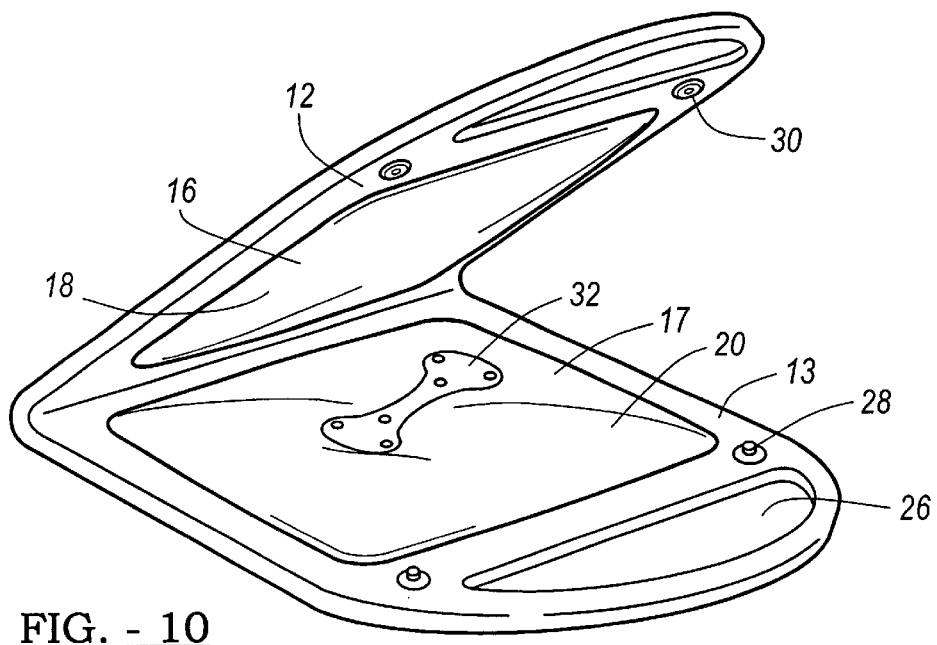
FIGS. 10–11 represent the incorporation of a polymer device into the resorbable implant heating device.
Figure 11:
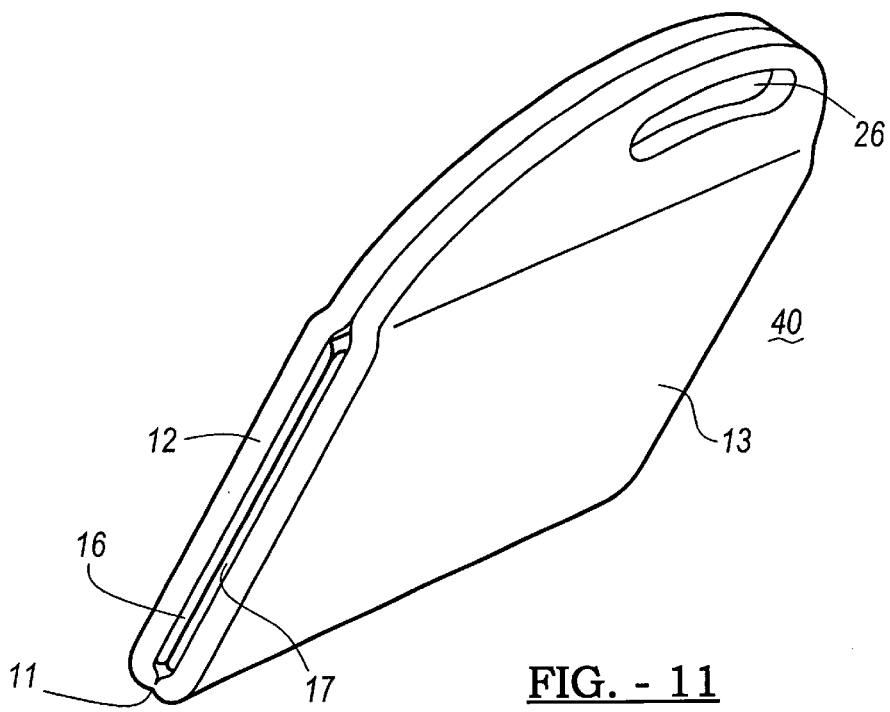

Insertion of the resorbable polymer implant 32 is depicted in FIGS. 10–11. In practice, the resorbable implant heating devices 10, 40, and 60 could each be placed within an autoclave until needed. After insertion of the resorbable polymer implant 32, the resorbable implant heating device 10, 40, or 60 is closed about the resorbable polymer implant 32. The resorbable implant heating device 10, 40, or 60 can additionally be wrapped in towels to maintain the heat. It should also be noted that the implant 32 may be positioned within the heating devices 10, 40, and 60 before the heating device is heated. It should also be noted that the heating device 10, 40, or 60 may eliminate its corresponding hinge such that each member of the heating device is separate and subsequently attached, via the fastening devices.

A wide variety of features can be utilized in the various materials disclosed and described above. The foregoing discussion discloses and describes a preferred embodiment of the present invention. One skilled in the art will readily recognize from such discussion, and from the accompanying drawings and claims, that various changes, modifications, and variations can be made therein without departing from the true spirit and fair scope of the invention.

What is claimed is:

1. A method for heating a polymer resorbable implant comprising:

providing a heating device having first and second members coupled together, said first member comprising a sealed cavity containing a liquid capable of storing heat, wherein said first and second members are rotatable about a hinge to place the sealed cavity adjacent said second member;

positioning said resorbable polymer implant on said first member;

positioning the first and second members adjacent each other, said polymer resorbable implant being positioned therebetween and adjacent the sealed cavity; and heating the liquid to above a glass transition temperature of the resorbable polymer implant.

2. The method of heating a polymer resorbable implant of claim 1 further comprising applying microwaves to the heating device so as to heat the liquid.

3. The method of heating a polymer resorbable implant of claim 1 wherein providing a heating device includes providing a heating device comprising a coupling device configured to hold the first member generally parallel to the second member.

4. The heating device of claim 1 wherein the step of providing a heating device includes providing a heating device with a first flexible member disposed over and sealably coupled to said first member, the first flexible member having a high heat transfer coefficient.

5. The method of claim 1 wherein said liquid has a boiling point of greater than about 220° F.

6. The method of claim 1 further comprising implanting the polymer resorbable implant into a patient.

7. The method of claim 1 wherein said first and second members are generally planar and the fastening device is one of a hook and loop fasteners and a snap.

8. The method of claim 1 wherein said first and second members define a handle.

9. The method of claim 1 wherein the step of providing said heating device includes providing a second member having a second inner surface and a second outer surface and defining a second cavity therebetween; and wherein the method further comprises inserting a fluidized bag within the second cavity.

10. The method of claim 1 wherein said first and second members comprise an insulating layer.

11. The method of claim 1 further comprising placing the heating device within an autoclave.

12. The method of claim 1 wherein the step of heating the liquid is heating the liquid to a temperature greater than about 220° F.

13. The method of claim 1 wherein providing a heating device is providing a heating device comprising a first sealed fluidized bag which is enclosed by said first member and a flexible member attached to said first member.

* * * * *